(12) United States Patent
Mukai

(10) Patent No.: US 8,225,647 B2
(45) Date of Patent: Jul. 24, 2012

(54) ABNORMALITY DIAGNOSIS APPARATUS FOR INTERNAL COMBUSTION ENGINE

(75) Inventor: Yasuo Mukai, Kariya (JP)

(73) Assignee: Denso Corporation, Kariya (JP)

( * ) Notice: Subject to any disclaimer, the term of this patent is extended or adjusted under 35 U.S.C. 154(b) by 443 days.

(21) Appl. No.: 12/486,242

(22) Filed: Jun. 17, 2009

(65) Prior Publication Data

US 2009/0314071 A1 Dec. 24, 2009

(30) Foreign Application Priority Data

Jun. 23, 2008 (JP) ................. 2008-162749
Jun. 23, 2008 (JP) ................. 2008-162750

(51) Int. Cl.
*G01M 15/04* (2006.01)
(52) U.S. Cl. ..................... 73/114.55
(58) Field of Classification Search ........... 73/114.38, 73/114.52, 114.55
See application file for complete search history.

(56) References Cited

U.S. PATENT DOCUMENTS

| 6,321,721 B1* | 11/2001 | Okumura et al. | 123/491 |
| 6,474,308 B2* | 11/2002 | Okumura et al. | 123/491 |
| 7,983,831 B2* | 7/2011 | Tsunooka | 701/104 |
| 2002/0023623 A1* | 2/2002 | Okumura et al. | 123/491 |
| 2004/0182378 A1* | 9/2004 | Oshimi et al. | 123/685 |
| 2008/0040018 A1 | 2/2008 | Katoch | |

FOREIGN PATENT DOCUMENTS

| JP | 2005-48625 | 2/2005 |
| JP | 2006-152990 | 6/2006 |
| JP | 2008-14160 | 1/2008 |
| WO | WO 2006/129198 | 12/2006 |

OTHER PUBLICATIONS

Commission Regulation (EC), Implementing and Amending Regulation (EC) No. 715/2007 of the European Parliament and of the Council of Jun. 20, 2007 on type-approval of motor vehicles with respect to emissions from light passenger and commercial vehicles (Euro 5 and Euro 6) and on access to vehicle repair and maintenance information, pp. 1-157 and deleted pages (2 pp.).

* cited by examiner

Primary Examiner — Eric S McCall
(74) Attorney, Agent, or Firm — Nixon & Vanderhye P.C.

(57) ABSTRACT

An alcohol concentration sensor detecting alcohol concentration of fuel is provided in a fuel tank or a fuel passage. An alcohol concentration detected at a previous driving of an engine is stored in a backup RAM. When a current alcohol concentration is different from the previous alcohol concentration, a procedure of an abnormality diagnosis is prohibited or invalidated until all of the fuel remaining in the fuel passage is consumed.

7 Claims, 6 Drawing Sheets

ABNORMALITY DIAGNOSIS APPARATUS FOR INTERNAL COMBUSTION ENGINE

CROSS-REFERENCE TO RELATED APPLICATION

This application is based on Japanese Patent Applications No. 2008-162749 filed on Jun. 23, 2008, and No. 2008-162750 filed on Jun. 23, 2008, the disclosures of which are incorporated herein by reference.

FIELD OF THE INVENTION

The present invention relates to an abnormality diagnosis apparatus for an internal combustion engine provided with a fuel property detecting means for detecting a fuel property (alcohol concentration, or a degree of heavy/light) supplied to a fuel injector from a fuel tank. The present invention also relates to an abnormality diagnosis apparatus for an internal combustion engine provided with a fuel property estimating means for estimating the fuel property based on a control condition of the internal combustion engine which varies due to the fuel property.

BACKGROUND OF THE INVENTION

Gasoline, alcohol, and mixed fuel of gasoline and alcohol are used as fuel for an internal combustion engine in order to reduce CO2 emissions and utilize petroleum substitute fuel. When the mixed fuel of which alcohol concentration has varied is supplied to a fuel tank, the alcohol concentration of the fuel in the fuel tank is varied. Since the stoichiometric air-fuel ratio is different between gasoline and alcohol, when the alcohol concentration is varied in the fuel tank, the stoichiometric air-fuel ratio of the fuel is also varied. Thus, it is necessary to vary the fuel injection quantity (actual air-fuel ratio) according to the alcohol concentration of the fuel.

JP-2006-152990A shows an engine control system in which an alcohol concentration sensor detecting alcohol concentration of the fuel is provided in a fuel passage between a fuel tank and a fuel injector.

However, such an alcohol concentration sensor increases costs of the system. In order to restrict an increase in costs, JP-2007-9903A (WO-2006/129198A1), JP-2005-48625A, and JP-2008-14160A show an engine control system in which an alcohol concentration of the fuel combusted in an internal combustion engine is estimated based on any one of an air-fuel ratio feedback control condition (for example, an air-fuel ratio feedback correction value, a deviation in air-fuel ratio, a ratio between a target air-fuel ratio and an actual air-fuel ratio, and the like), a fuel pressure increasing speed during starting period of the engine, a combustion stability (fluctuation in engine speed), an engine torque, and the like.

Besides, a highly electronically-controlled engine control system, as shown in JP-2008-38785A (US-2008/0040018A1), is provided with diagnosis functions, such as fuel system abnormality diagnosis, catalyst deterioration diagnosis, air-fuel ratio control diagnosis, combustion condition diagnosis (detection of misfire) and the like.

In a case that an engine control system provided with an alcohol concentration sensor has diagnosis functions described above, following problems will arise. When a fuel of which alcohol concentration is different from previously filled fuel is supplied to a fuel tank so that the alcohol concentration of the fuel in the fuel tank is varied, after starting the engine, the fuel remaining in a fuel passage between the fuel tank and the fuel injector is initially supplied to the fuel injector. Then, when the remaining fuel is consumed and the fuel in the fuel tank is supplied to the fuel injector through the fuel passage, the alcohol concentration of the fuel injected from the injector is rapidly changed, whereby an air excess ratio (=air-fuel ratio/stoichiometric air-fuel ratio) will be rapidly changed in a lean direction or a rich direction.

Since the alcohol concentration sensor is disposed in the fuel passage between the fuel tank and the fuel injector or in the fuel tank (for example, in a fuel pump), during a period from a time when the alcohol concentration sensor detects varied alcohol concentration to a time when the fuel remaining in the fuel passage between the alcohol concentration sensor and the fuel injector is totally consumed, the alcohol concentration detected by the alcohol concentration sensor is different from the alcohol concentration of the fuel actually injected from the injector.

The fuel system abnormality diagnosis, the catalyst deterioration diagnosis, the air-fuel ratio control diagnosis, and the combustion condition diagnosis is respectively performed based on parameters which vary due to the alcohol concentration of the fuel. Thus, when the alcohol concentration detected by the alcohol concentration sensor is different from the alcohol concentration of the fuel actually injected from the injector, there is a possibility that an erroneous determination may be made in each diagnosis. Such problems arise also in a case that a fuel weight sensor detecting a weight degree of fuel (heavy/light) is provided in a fuel passage or a fuel tank and the varied weight fuel is supplied to the fuel tank.

In a case that an engine control system provided with an alcohol concentration estimating device has diagnosis functions described above, following problems will arise. The fuel system abnormality diagnosis, the catalyst deterioration diagnosis, the air-fuel ratio control diagnosis, and the combustion condition diagnosis is respectively performed based on parameters which vary due to the alcohol concentration of the fuel, such as an air excess ratio (=air-fuel ratio/stoichiometric air-fuel ratio), a fluctuation in engine speed and the like. Thus, when each of the diagnoses is performed, information about alcohol concentration of fuel is necessary. However, since it takes a long time for an engine driving condition to become a stable condition where the alcohol concentration can be estimated, the alcohol concentration can not be estimated for a while after starting of engine. For example, in a case that the alcohol concentration is estimated based on an air-fuel ratio feedback control condition (for example, an air-fuel ratio feedback correction value, a deviation in air-fuel ratio, a ratio between a target air-fuel ratio and an actual air-fuel ratio, and the like), the alcohol concentration can not be estimated until an exhaust gas senor (air-fuel ratio sensor, or oxygen sensor) in an exhaust passage is activated to perform an air-fuel ratio feedback control.

To avoid such an inconvenience, it can be conceivable that a previously estimated alcohol concentration is tentatively used as a current estimated alcohol concentration until the engine driving condition becomes stable. However, until the engine driving condition becomes stable, each diagnosis is performed based on an incorrect alcohol concentration. Thus, an erroneous diagnosis may be performed. Such problems arise also in a system where a weight degree of fuel (heavy/light) is estimated and specified diagnoses are performed based on the weight degree of fuel.

SUMMARY OF THE INVENTION

The present invention is made in view of the above matters, and it is an object of the present invention to provide an abnormality diagnosis apparatus for an internal combustion engine, which is capable of avoiding an erroneous diagnosis to improve a credibility of the abnormality diagnosis even if fuel of which property is varied is supplied.

According to the present invention, an abnormality diagnosis apparatus includes a fuel property detecting means for detecting a property of a fuel supplied from a fuel tank to a fuel injector. The abnormality diagnosis apparatus performs an abnormality diagnosis with respect to a specified object based on the property of the fuel. Further, the abnormality diagnosis apparatus includes an erroneous diagnosis preventing means for prohibiting or invalidating processes of the abnormality diagnosis until a specified time period has passed when a currently detected property of the fuel is different from a previously detected property of the fuel.

According to another aspect of the invention, an abnormality diagnosis may be performed with respect to a specified object by use of an abnormality threshold which is established according to a previously detected property of the fuel until a specified time period has passed when a currently detected property of the fuel is different from the previously detected property of the fuel.

According to another aspect of the invention, an abnormality diagnosis apparatus includes a fuel property estimating means for estimating a fuel property based on an engine control condition which varies due to the fuel property. An abnormality diagnosis is performed with respect to a specified object based on the fuel property. The abnormality diagnosis apparatus includes a nonvolatile memory means for storing the estimated fuel property. The abnormality diagnosis apparatus further includes an erroneous diagnosis preventing means for invalidating processing data of the abnormality diagnosis which has been executed from a starting of the engine until it becomes apparent that a currently estimated fuel property is different from a previously estimated fuel property stored in the nonvolatile memory means.

BRIEF DESCRIPTION OF THE DRAWINGS

Other objects, features and advantages of the present invention will become more apparent from the following description made with reference to the accompanying drawings, in which like parts are designated by like reference numbers and in which.

DETAILED DESCRIPTION OF EMBODIMENTS

Embodiments of the present invention will be described hereinafter.

First Embodiment

Figure 1:
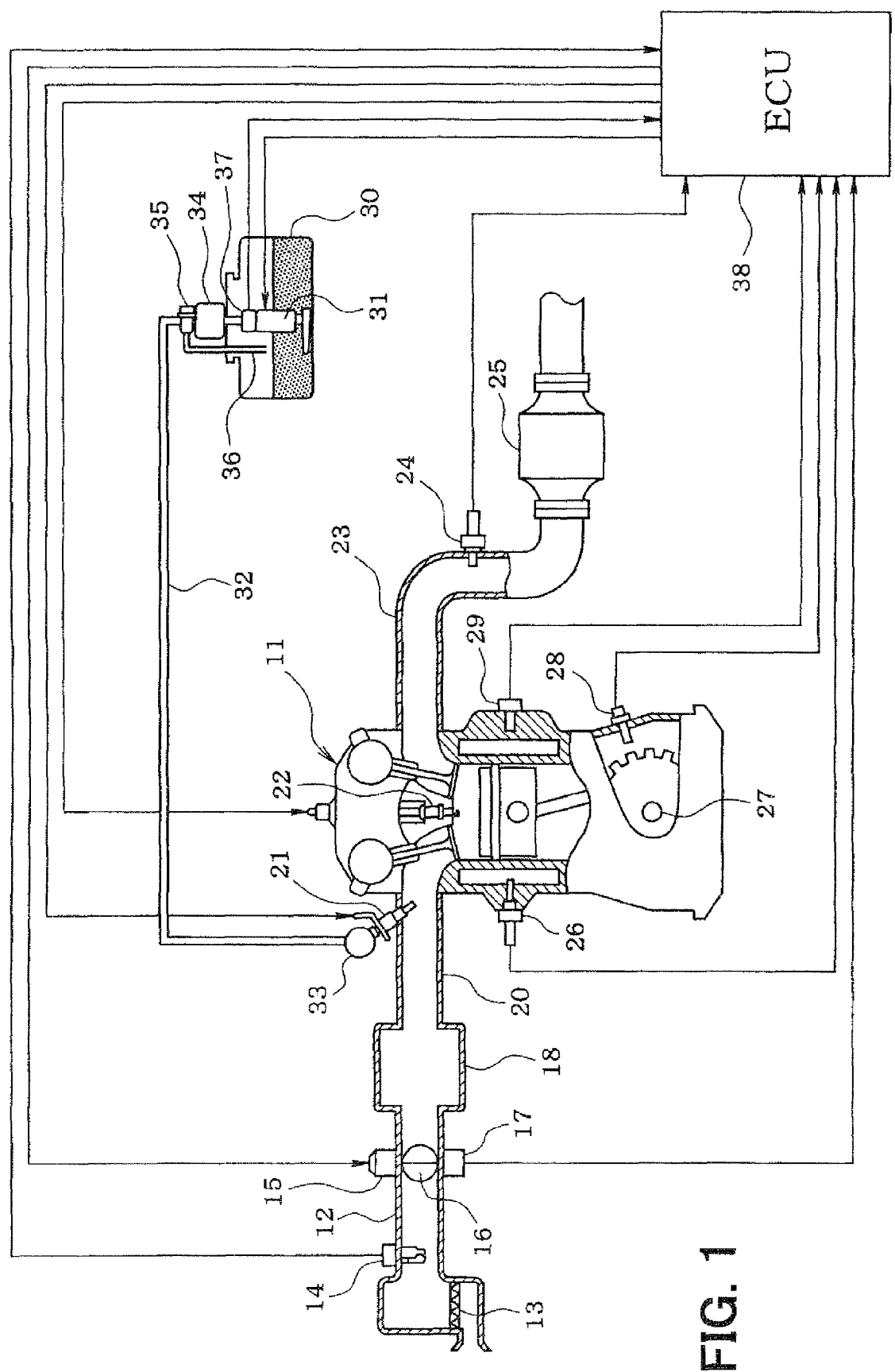
FIG. 1 is a schematic view of an engine control system according to a first and a second embodiment of the present invention.
Figure 2:
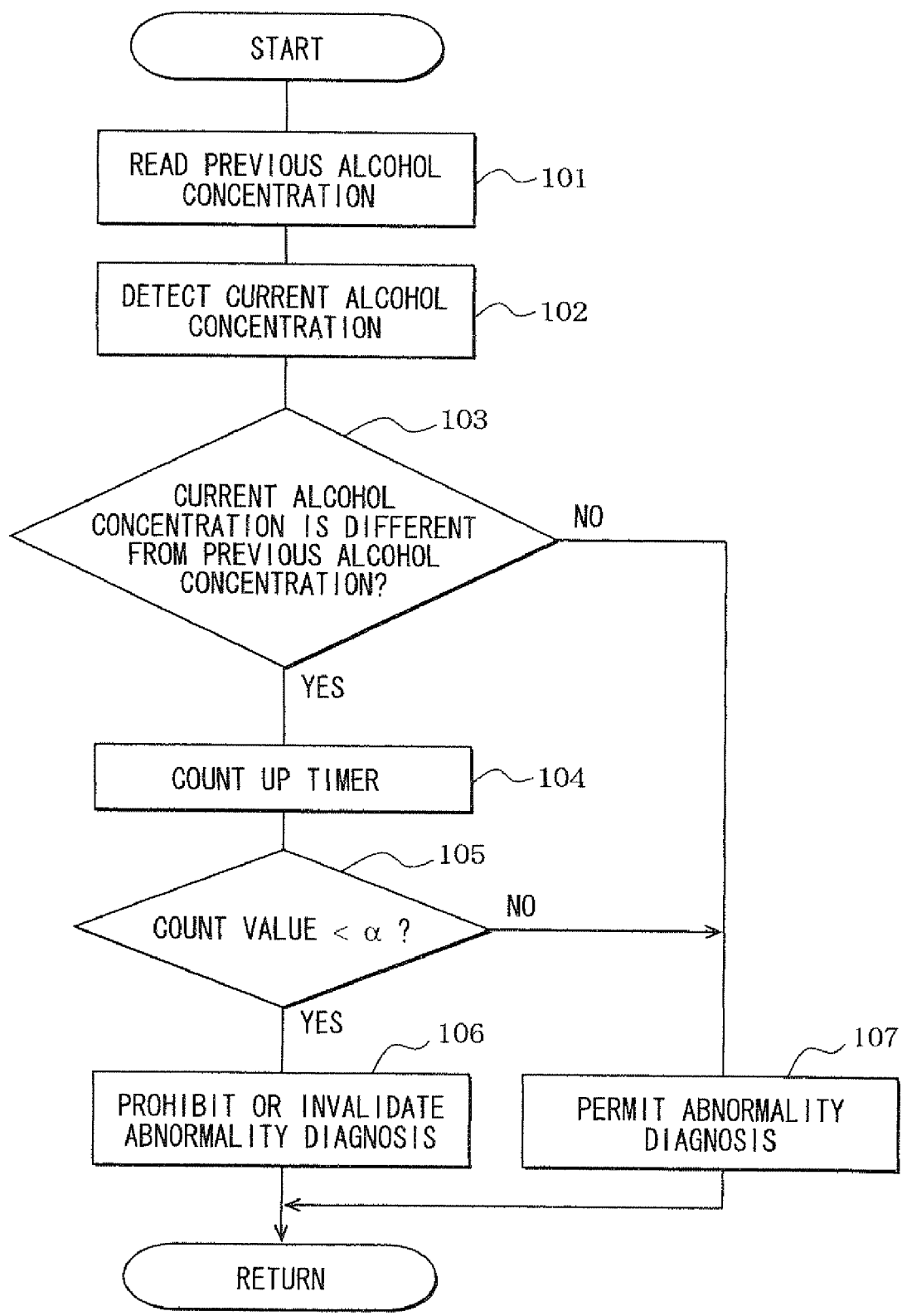
FIG. 2 is a flowchart showing a process of a program for determining whether an abnormality diagnosis can be performed according to the first embodiment.

Referring to FIGS. 1 and 2, a first embodiment will be described hereinafter.

Referring to FIG. 1, an engine control system is explained. An air cleaner 13 is arranged upstream of an intake pipe 12 of an internal combustion engine 11. An airflow meter 14 detecting an intake air flow rate is provided downstream of the air cleaner 13. A throttle valve 16 driven by a DC-motor 15 and a throttle position sensor 17 detecting a throttle position (throttle opening degree) are provided downstream of the air flow meter 14.

A surge tank 18 is provided downstream of the throttle valve 16. An intake air manifold 20 is connected to the surge tank 18 to introduce air into the engine 11. A fuel injector 21 is provided at a vicinity of an intake air port of the intake manifold of each cylinder to inject fuel into the cylinder. A spark plug 22 is mounted on a cylinder head of the engine 11 corresponding to each cylinder to ignite air-fuel mixture in each cylinder.

An exhaust gas sensor (an air fuel ratio sensor, an oxygen sensor) 24 which detects an air-fuel ratio of the exhaust gas is respectively provided in each exhaust pipe 23, and a three-way catalyst 25 which purifies the exhaust gas is provided downstream of the exhaust gas sensor 24.

A coolant temperature sensor 26 detecting a coolant temperature and a knock sensor 29 detecting knocking of the engine are disposed on a cylinder block of the engine 11. A crank angle sensor 28 is installed on a cylinder block to output crank angle pulses when a crank shaft 27 rotates a predetermined angle. Based on this crank angle pulses, a crank angle and an engine speed are detected.

The engine 11 can use gasoline, alcohol such as ethanol and methanol, or mixture fuel of gasoline and alcohol. Any one of gasoline, alcohol, and mixture fuel is supplied to a fuel tank 30. A fuel pump 31 which pumps up the fuel is provided in the fuel tank 30. The fuel discharged from the fuel pump 31 is sent to the delivery pipe 33 through the fuel pipe 32 and is distributed to the fuel injector 21 of each cylinder from this delivery pipe 33. A fuel filter 34 and a pressure regulator 35 are connected to the fuel pipe 32 at a vicinity of the fuel pump 31. A discharge pressure of the fuel pump 31 is adjusted to a predetermined pressure by the pressure regulator 35. A surplus of the fuel exceeding the predetermined pressure is returned to the fuel tank 30 through a fuel-return pipe 36.

An alcohol concentration sensor 37 (fuel property detecting means) detecting an alcohol concentration of the fuel discharged from the fuel pump 31 is provided in the fuel tank 30. Since the alcohol concentration sensor 37 is provided in the fuel tank 30, the leaked fuel is returned to the fuel tank 30 even if the fuel is leaked from the alcohol concentration sensor 37 due to the faulty of the alcohol concentration sensor 37. Alternatively, the alcohol concentration sensor 37 may be provided in the fuel pipe 32 or the delivery pipe 33. Any type of alcohol concentration sensor can be used. For example, a capacitance type alcohol concentration sensor or an optical type alcohol concentration sensor can be used.

The outputs of the sensors, such as the exhaust gas sensor 24, are inputted to an electronic control unit (ECU) 38. The ECU 38 includes a microcomputer which executes an engine control program stored in a Read Only Memory (ROM) to control a fuel injection quantity of a fuel injector 21 and an ignition timing of a spark plug 22 according to an engine running condition.

As the alcohol concentration of the fuel becomes higher, the stoichiometric air-fuel ratio of the fuel becomes smaller and the fuel injection quantity increases for controlling the actual air-fuel ratio to the stoichiometric air-fuel ratio. Based on this relationship, the ECU 38 performs a fuel injection control program (not shown) to increasingly correct the fuel injection quantity according to the alcohol concentration in such a manner that the fuel injection quantity increases as the alcohol concentration detected by the sensor 37 becomes higher.

Furthermore, the ECU 38 executes various abnormality diagnosis programs to perform abnormality diagnoses, such as fuel system abnormality diagnosis, catalyst deterioration diagnosis, air-fuel ratio control diagnosis, combustion condition diagnosis (detection of misfire) and the like. Since each of the abnormality diagnoses is performed by use of parameters (for example, an air excess ratio, a fluctuation in engine speed) which vary due to the alcohol concentration of the fuel, an abnormality determination threshold is established according to the alcohol concentration detected by the alcohol concentration sensor 37.

When the mixed fuel of which alcohol concentration has varied is supplied to a fuel tank 30, the alcohol concentration of the fuel in the fuel tank 30 is varied. In such a case, the fuel remaining in the fuel pipe 32 and the delivery pipe 33 between the fuel tank 30 and the fuel injector 21 is initially supplied to the fuel injector 21. Then, after the fuel remaining in the fuel passage is consumed, the fuel in the fuel tank 30 is supplied to the fuel injector 21 through the fuel passage. At this time, the alcohol concentration of the fuel injected from the injector 21 is rapidly changed and an air excess ratio (=air-fuel ratio/stoichiometric air-fuel ratio) may rapidly vary in learn direction or rich direction.

Since the alcohol concentration sensor 37 is disposed in the fuel tank 30 or in the fuel passage between the fuel tank 30 and the fuel injector 21, during a period from a time when the alcohol concentration sensor 37 detects varied alcohol concentration to a time when the fuel remaining in the fuel passage between the alcohol concentration sensor 37 and the fuel injector 21 is totally consumed, the alcohol concentration detected by the alcohol concentration sensor 37 is different from the alcohol concentration of the fuel actually injected from the injector 21.

As described above, the fuel system abnormality diagnosis, the catalyst deterioration diagnosis, the air-fuel ratio control diagnosis, and the combustion condition diagnosis are respectively performed based on parameters which vary due to the alcohol concentration of the fuel, such as an air excess ratio, a fluctuation in engine speed and the like. Thus, an erroneous diagnosis may be made if the alcohol concentration detected by the alcohol concentration sensor 37 is different from the alcohol concentration of the fuel injected from the fuel injector 21.

According to the first embodiment, the ECU 38 executes a program for determining whether an abnormality diagnosis can be performed, which is shown in FIG. 2. Thereby, if a present alcohol concentration detected by the sensor 37 is different from a previous alcohol concentration detected by the sensor 37, each abnormality diagnosis is prohibited or invalidated until a specified time has passed. This specified period is established longer than or equal to a time period which is necessary for the fuel remaining in the fuel passage between the alcohol concentration sensor 37 and the fuel injector 21 to be injected.

Referring to FIG. 2, the processes of the program for determining whether an abnormality diagnosis can be performed will be described below. This program is executed at a specified time interval while an ignition switch is ON (the ECU 38 is ON), and corresponds to an erroneous diagnosis preventing means.

In step 101, a previous alcohol concentration is read, which is stored in a nonvolatile memory such as a backup RAM of the ECU 38. This previous alcohol concentration is an alcohol concentration detected by the alcohol concentration sensor 37 and stored in the memory at a time of previous driving of the engine (for example, at a time after specified time has passed from starting of the engine or at a time of shutting down of the previous driving).

Then, the procedure proceeds to step 102 in which a current alcohol concentration at a current driving of the engine is detected by the alcohol concentration sensor 37. Then, the procedure proceeds to step 103 in which the computer determines whether the current alcohol concentration is different from the previous alcohol concentration. When the current alcohol concentration agrees with the previous alcohol concentration, the procedure proceeds to step 107 in which the abnormality diagnosis is permitted to be performed. When the other diagnosis executing condition is established, the abnormality diagnosis is started to be performed.

When the computer determines that the current alcohol concentration is different from the previous alcohol concentration in step 103, the procedure proceeds to step 104 in which a timer is counted up. Then, in step 105, the computer determines the count value of the timer is less than a predetermined value $\alpha$. This predetermined value $\alpha$ is established longer than or equal to a time period which is necessary for all of the fuel remaining in the fuel passage between the alcohol concentration sensor 37 and the fuel injector 21 to be injected.

Alternatively, instead of the processes in steps 104 and 105, the computer may determine whether an integrated fuel injection quantity is less than a fuel injection quantity which is equal to a fuel quantity remaining in the fuel passage between the alcohol concentration sensor 37 and the fuel injector 21.

When the answer is Yes in step 105, the computer determines that the previous fuel is still remaining in the fuel passage between the alcohol concentration sensor 37 and the fuel injector 21, and the procedure proceeds to step 106 in which each abnormality diagnosis is prohibited or invalidated. In this case, even if the other diagnosis executing conditions are established, the abnormality diagnosis is not performed. If the abnormality diagnosis has been already performed, the process is stopped or invalidated so that the diagnosis result is invalidated.

The above processes are repeatedly performed at a specified time period. When the current alcohol concentration is different from the previous alcohol concentration, until the count value of the timer becomes greater than or equal to the specified value $\alpha$, the abnormality diagnosis is prohibited or invalidated. When the count value of the timer becomes grater than or equal to the specified value $\alpha$, it is determined that the previous fuel remaining in the fuel passage between the alcohol concentration sensor 37 and the fuel injector 21 has been injected, the procedure proceeds from step 105 to step 107 in which the abnormality diagnosis is permitted. Then, when the other diagnosis executing condition is established, the abnormality diagnosis is performed.

According to the first embodiment, since the abnormality diagnosis is prohibited or invalidated in a case that the current alcohol concentration is different from the previous alcohol concentration, an erroneous diagnosis can be avoided to improve a credibility of the abnormality diagnosis.

Second Embodiment

Figure 3:
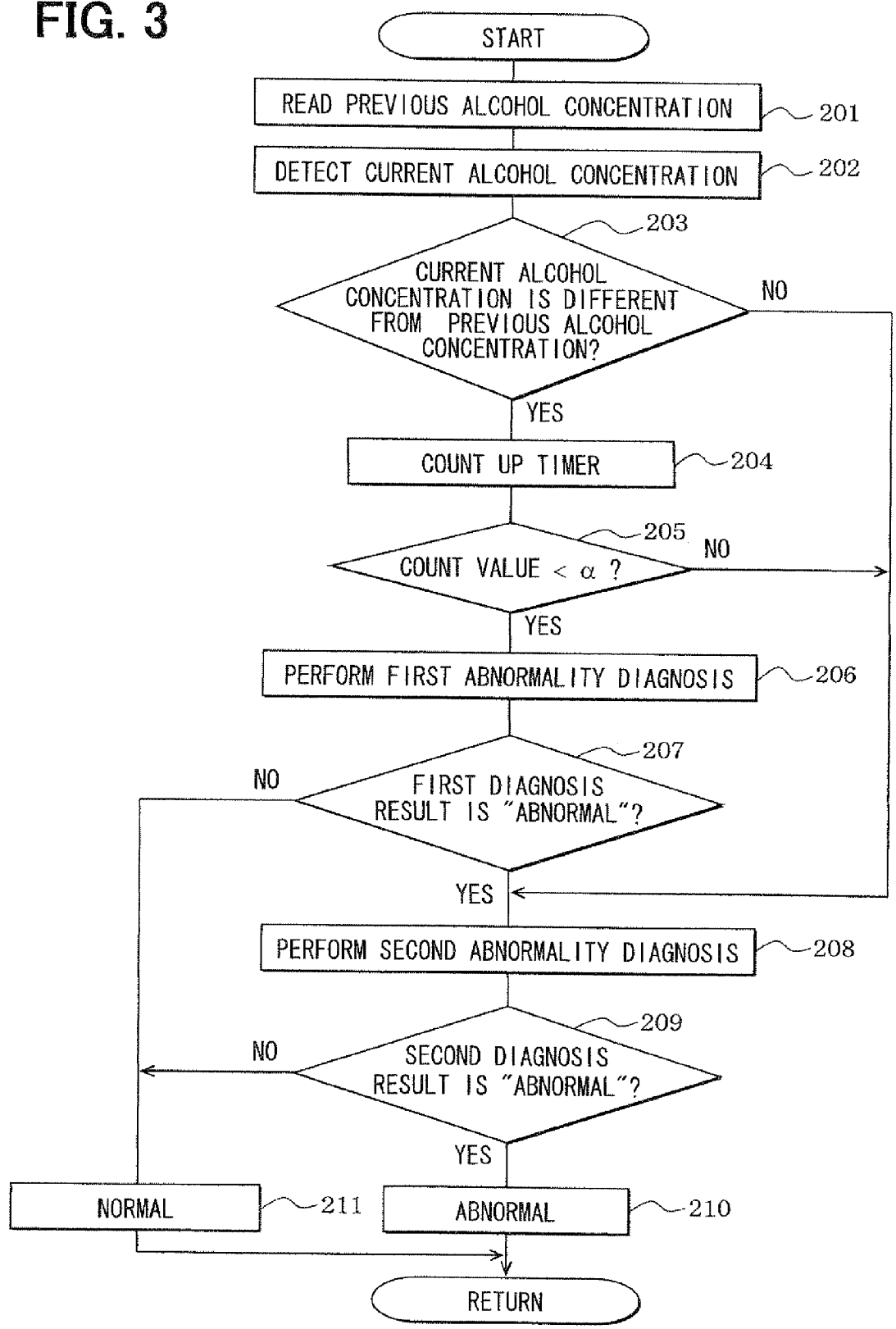
FIG. 3 is a flowchart showing a process of a program for determining whether an abnormality diagnosis can be performed according to the second embodiment.

In a second embodiment, the computer executes a program for determining whether an abnormality diagnosis can be performed, which is shown in FIG. 3. In a case that the current alcohol concentration is different from the previous alcohol concentration, a first abnormality diagnosis is performed until a specified time period has passed by use of a first threshold which is determined based on the previous alcohol concentration. When the computer determines that an abnormality exists in the first abnormality diagnosis, a second abnormality diagnosis is performed by use of a second threshold which is determined based on the current alcohol concentration. When the computer determines that an abnormality exists also in the second abnormality diagnosis, the computer finally determines that an abnormality exists.

Referring to FIG. 3, the processes of the program for determining whether an abnormality diagnosis can be performed will be described below. This program is executed at a specified time interval while an ignition switch is ON (the ECU 38 is ON), and corresponds to an erroneous diagnosis preventing means.

The processes in steps 201-205 are the same processes in steps 101-105 in FIG. 2. The previous alcohol concentration is read from the memory in step 201 and the current alcohol concentration is detected by the alcohol concentration sensor 37 in step 202. Then, when the computer determines that the current alcohol concentration is different from the previous alcohol concentration in step 203, the procedure proceeds to step 204 in which a timer is counted up. Until the counter value of the timer becomes greater than a specified value α, the procedure proceeds from step 205 to step 206 in which the first abnormality diagnosis is performed by use of the first threshold which is determined according to the previous alcohol concentration.

Then, the procedure proceeds to step 207 in which the computer determines whether a first diagnosis result is "abnormal". When the answer is No in step 207, the procedure proceeds to step 211 in which the computer determines that the diagnosis result is "normal" to end the routine.

When the answer is Yes in step 207, the procedure proceeds to step 208 in which the second abnormality diagnosis is performed by use of the second threshold which is established according to the current alcohol concentration.

Then, the procedure proceeds to step 209 in which the computer determines whether the second diagnosis result is "abnormal". When the answer is No in step 209, the procedure proceeds to step 211 in which the computer determines that the diagnosis result is "normal" to end the routine. If the second diagnosis result is "abnormal" in step 209, the procedure proceeds to step 210 in which the computer determines that the diagnosis result is finally "abnormal".

When the answer is No in step 205, the procedure proceeds to step 208 in which the second abnormality diagnosis is performed by use of the second threshold. The diagnosis result of the second abnormality diagnosis is made as the final diagnosis result. The other processes are the same as the first embodiment.

Alternatively, when the current alcohol concentration is different from the previous alcohol concentration, only first abnormality diagnosis is performed and the second abnormality diagnosis can be omitted.

According to the second embodiment, when the current alcohol concentration is different from the previous alcohol concentration, the abnormality diagnosis is performed by use of a threshold which is established based on the previous alcohol concentration until a specified period has passed. Thus, an erroneous diagnosis can be avoided and the abnormality diagnosis can be performed quickly after starting of the engine.

Furthermore, according to the second embodiment, a final diagnosis result is made based on a diagnosis result by use of a first threshold established according to the previous alcohol concentration and a diagnosis result by use of a second threshold established according to the current alcohol concentration. Thus, even if fuel of which alcohol concentration is varied is supplied, the abnormality diagnosis can be correctly performed.

In the above embodiments, an alcohol concentration sensor 37 is used as a fuel property detecting means. Alternatively, a fuel weight sensor detecting fuel weight can be provided in the fuel tank 30, the fuel pipe 32 or delivery pipe 33. If a current fuel weight is different from a previous fuel weight, the abnormality diagnosis may be prohibited or invalidated. Alternatively, in a case that current fuel weight is different from the previous fuel weight, the abnormality diagnosis can be performed by use of a threshold which is established according to the previous fuel property until a specified time period has passed. Alternatively, in a case that current fuel weight is different from the previous fuel weight, a final diagnosis result can be made based on a diagnosis result by use of a threshold which is established according to the previous fuel weight and a diagnosis result by use of a threshold which is established according to the current fuel weight.

Third Embodiment

In the third and the successive embodiments, the same parts and components as those in the first and the second embodiments are indicated with the same reference numerals and the same descriptions will not be reiterated.

Figure 4:
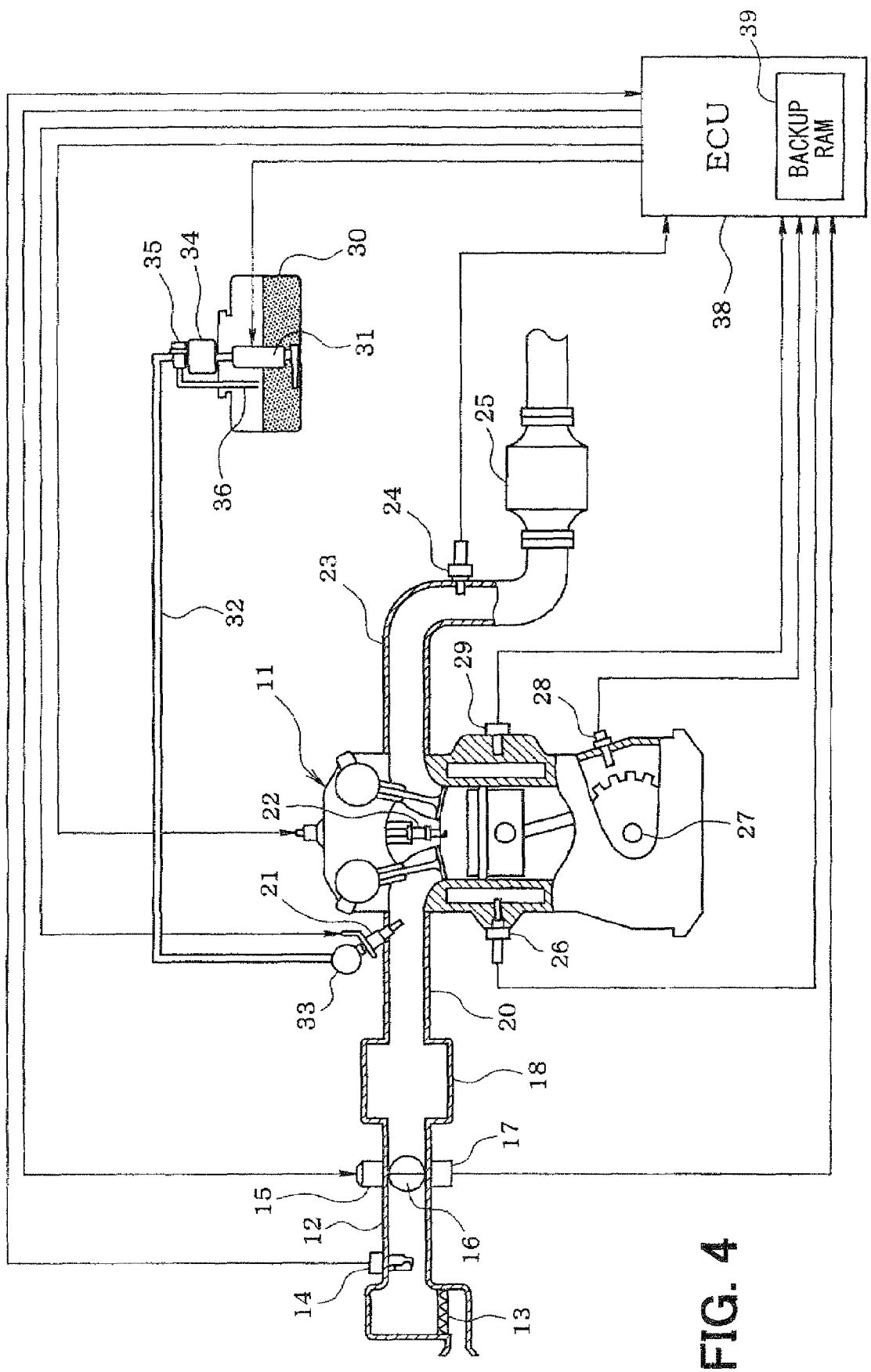
FIG. 4 is a schematic view of an engine control system according to a third and a fourth embodiment of the present invention.

As shown in FIG. 4, outputs of the various sensors, such as the exhaust sensor 24, are inputted into ECU 38. The ECU 38 performs an air-fuel-ratio feedback control program stored in the ROM so that the air-fuel ratio (fuel injection quantity) is feedback controlled to agree with a target air-fuel ratio.

As the alcohol concentration of the fuel becomes higher, the stoichiometric air-fuel ratio of the fuel becomes smaller and the fuel injection quantity increases for controlling the actual air-fuel ratio to the stoichiometric air-fuel ratio. Based on an air-fuel ratio feedback control condition (for example, an air-fuel ratio feedback correction value, a deviation in air-fuel ratio, a ratio between a target air-fuel ratio and an actual air-fuel ratio, and the like), the ECU 38 estimates an alcohol concentration of the fuel combusted in the engine 11. The ECU 38 increasingly correct the fuel injection quantity according to the alcohol concentration in such a manner that the fuel injection quantity increases as the estimated alcohol concentration becomes higher. This alcohol concentration estimating function of the ECU 38 corresponds to a fuel property estimating means.

The alcohol concentration can be estimated based on any one of fuel pressure increasing speed, a combustion stability (fluctuation in engine speed), and an engine torque. That is, the alcohol concentration can be estimated based on a control condition of the engine which varies according to the alcohol concentration of the fuel.

Furthermore, the ECU 38 executes various abnormality diagnosis programs to perform abnormality diagnoses, such as fuel system abnormality diagnosis, catalyst deterioration diagnosis, air-fuel ratio control diagnosis, combustion condition diagnosis (detection of misfire) and the like. Since each of the abnormality diagnoses is performed by use of parameters (for example, an air excess ratio, a fluctuation in engine speed) which vary due to the alcohol concentration of the fuel, an abnormality determination threshold is established according to the estimated alcohol concentration. For example, in a case that the alcohol concentration is estimated based on an air-fuel ratio feedback control condition (for example, an air-fuel ratio feedback correction value, a deviation in air-fuel ratio, a ratio between a target air-fuel ratio and an actual air-fuel ratio, and the like), an alcohol concentration estimation executing condition is not established and the alcohol concentration can not be estimated until an exhaust gas sensor 21 is activated to perform an air-fuel ratio feedback control.

According to the present embodiment, the alcohol concentration estimated during an engine driving is stored in a non-volatile memory, such as the backup RAM 39. Until the alcohol concentration estimation executing condition is established, the engine control and the abnormality diagnoses are performed by use of the previously estimated alcohol concentration as the current alcohol concentration temporarily. Thus, even before the driving condition becomes a condition where the alcohol concentration can be estimated, the abnormality diagnosis can be performed by use of the previous alcohol concentration. The abnormality diagnosis can be performed quickly and an erroneous diagnosis can be avoided.

However, when the fuel of different alcohol concentration from last time was refueled to the fuel tank 30 and the alcohol concentration of the fuel in the fuel tank 30 varies, each abnormality diagnosis will be performed using the incorrect alcohol concentration until it will be in the operational status which can estimate alcohol concentration so that an erroneous diagnosis may be performed.

Figure 5:
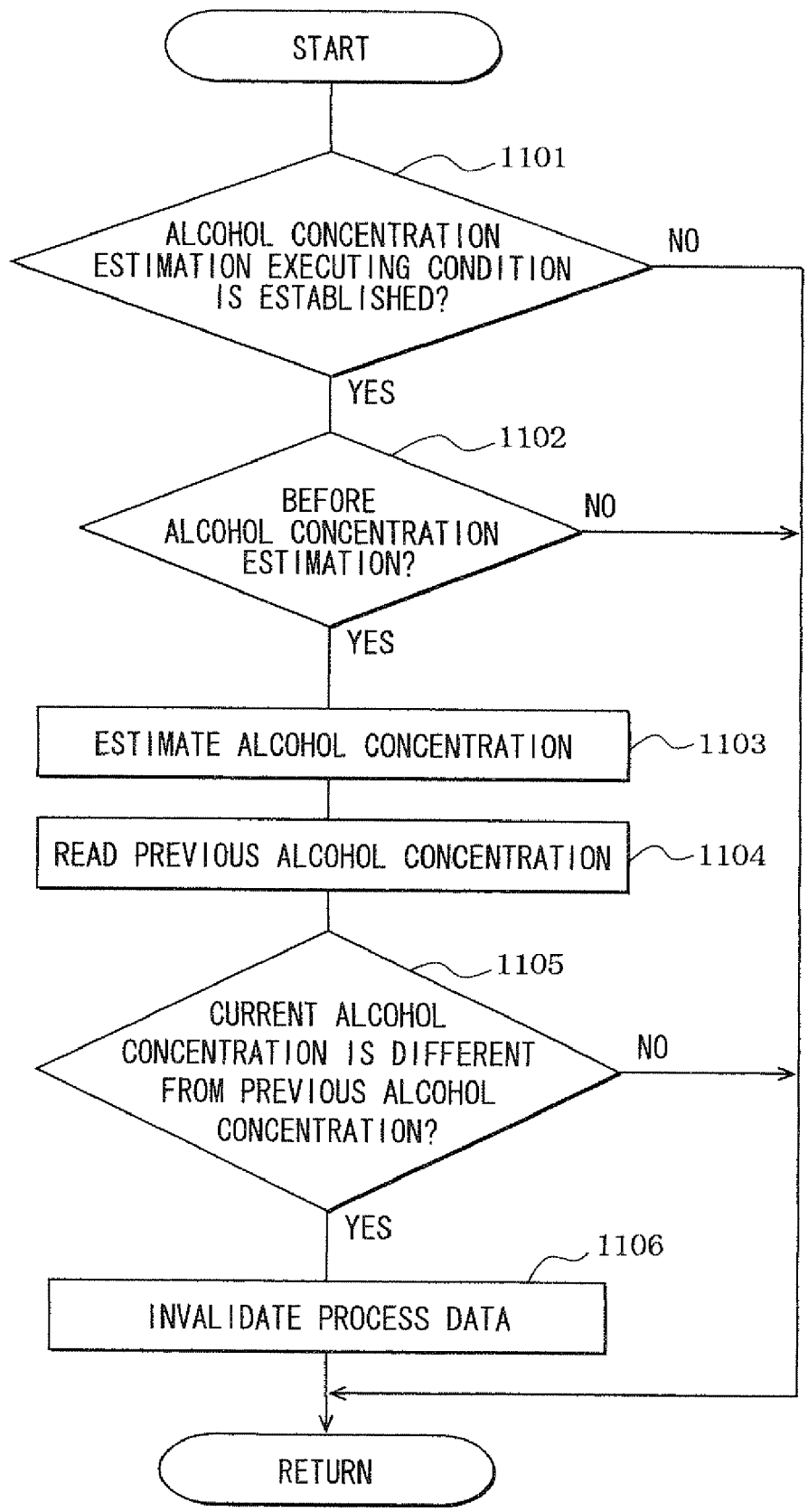
FIG. 5 is a flowchart showing a process of a program for preventing an erroneous diagnosis according to the third embodiment.

According to the present embodiment, the ECU 38 performs a program for preventing an erroneous diagnosis, which is shown in FIG. 5. When it becomes apparent that the currently estimated alcohol concentration is different from the previously estimated alcohol concentration stored in the backup RAM 39, process data of abnormality diagnosis (for example, diagnosis results, diagnosis processing data, learning data, and the like) which are executed from engine starting until that time are invalidated. That is, these process data are reset.

Referring to FIG. 5, the processes of the program for preventing an erroneous diagnosis will be described below. This program is executed at a specified time interval while an ignition switch is ON (the ECU 38 is ON), and corresponds to an erroneous diagnosis preventing means.

In step 1101, the computer determines whether the exhaust gas sensor 21 is activated to estimate the alcohol concentration. That is, the computer determines whether the alcohol concentration estimation executing condition is established. When the answer is No in step 1101, this program is ended without performing subsequent processes.

When the answer is Yes in step 1101, the procedure proceeds to step 1102 in which the computer determines whether it is before the alcohol concentration estimation. When the answer is No in step 1102, the program is ended without performing subsequent process.

When the answer is Yes in step 1102, the procedure proceeds to step 1103 in which the alcohol concentration of the fuel is estimated based on the controlling condition of the air-fuel ratio feedback control. Then, the procedure proceeds to step 1104 in which the computer reads the previous alcohol concentration stored in the backup RAM 39.

Then, the procedure proceeds to step 1105 in which the computer determines whether the current alcohol concentration is different from the previous alcohol concentration. When the answer is No in step 1105, that is, when the current alcohol concentration agrees with the previous alcohol concentration, the program is ended.

When the answer is Yes in step 1105, the procedure proceeds to step 1106 in which the processing data of abnormality diagnosis from starting of the engine are invalidated. That is, these processing data are reset. For example, the diagnosis results, diagnosis processing data (values stored in the RAM, flag value, and abnormality counter value), learning data, and the like are invalidated. These data are reset.

According to the present embodiment, since the abnormality diagnosis is prohibited or invalidated in a case that the currently estimated alcohol concentration is different from the previously estimated alcohol concentration, an erroneous diagnosis can be avoided to improve a credibility of the abnormality diagnosis.

Fourth Embodiment

When a fuel of which alcohol concentration is different from previously filled fuel is supplied to a fuel tank 30 so that the alcohol concentration of the fuel in the fuel tank 30 is varied, after starting the engine, the fuel remaining in a fuel passage (fuel pipe 32 and delivery pipe 33) between the fuel tank 30 and the fuel injector 21 is initially supplied to the fuel injector 21. Until the remaining fuel is consumed and the fuel in the fuel tank 30 is supplied to the fuel injector 21 through the fuel passage, the currently supplied fuel is not injected from the injector 21, so that the alcohol concentration after refuel can not be estimated.

In a case that the previous fuel is remaining in the fuel passage at a time when the alcohol concentration estimation executing condition is established, the previous fuel is injected from the fuel injector 21 for a while. Thus, the previous alcohol concentration is estimated.

Figure 6:
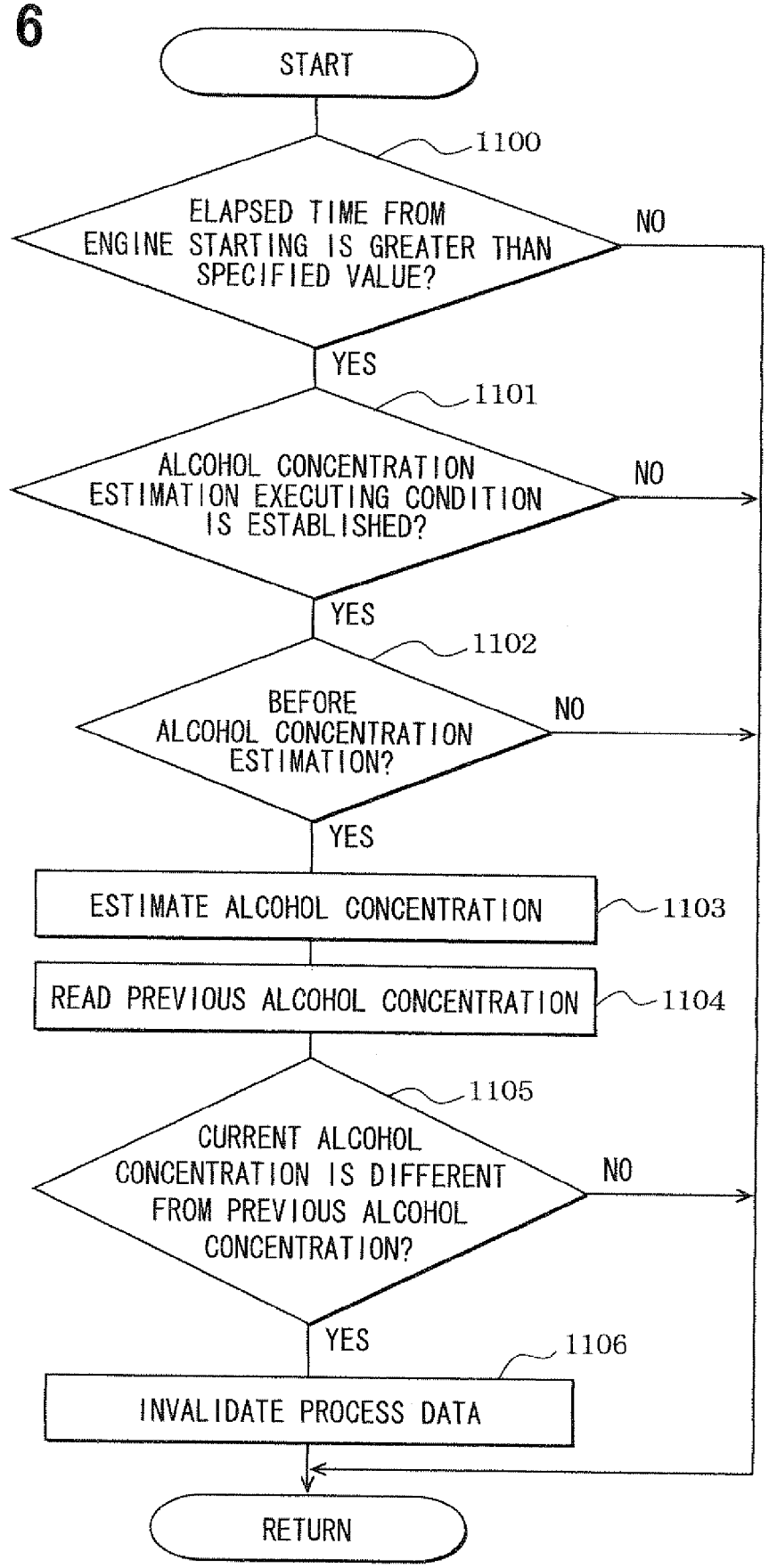
FIG. 6 is a flowchart showing a process of a program for preventing an erroneous diagnosis according to the fourth embodiment.

According to a fourth embodiment, the ECU 38 performs a program for preventing an erroneous diagnosis, which is shown in FIG. 6. Until all of the fuel remaining in the fuel passage is injected from the fuel injector 21, an alcohol concentration estimation is prohibited. The time period where the alcohol concentration estimation is prohibited is established based on an elapsed time after engine starting or an integral fuel injection quantity after engine starting.

The program shown in FIG. 6 is a program in which a processing of step 1100 is added to the program shown in FIG. 5. The other steps 1101-1106 are the same as those in FIG. 5.

This program shown in FIG. 6 is executed at a specified time interval while an ignition switch is ON (the ECU 38 is ON), and corresponds to an erroneous diagnosis preventing means.

In step 1100, the computer determines whether a specified time period has elapsed from starting of the engine. That is, the computer determines whether an elapsed time from engine starting is greater than a specified value. Alternatively, the computer determines whether integrated fuel injection quantity is greater than a specified value. This specified value is established longer than or equal to a time period or an integral fuel injection quantity which is necessary for the fuel remaining in the fuel passage to be injected. When the answer is No in step 1100, the program ends.

When the answer is Yes in step 1100, the procedure proceeds step 1101. The successive procedures in steps 1101-1106 are the same as those in FIG. 5.

According to the fourth embodiment, since the alcohol concentration estimation is prohibited until the all fuel remaining in the fuel passage is injected from the fuel injector 21, the fuel property after refueling can be correctly estimated.

In the above embodiments, the alcohol concentration of the fuel is estimated. Alternatively, the fuel weight may be estimated. When a current fuel weight is different from a previous fuel weight, the process data of the abnormality diagnosis is invalidated.

The present invention is not limited to an intake port injection engine. The present invention can be applied to a direct injection engine or a dual injection engine.

What is claimed is:

1. An abnormality diagnosis apparatus for an internal combustion engine, including a fuel property detecting unit configured to detect a property of a fuel supplied from a fuel tank to a fuel injector, the abnormality diagnosis apparatus performing an abnormality diagnosis with respect to a specified object based on the property of the fuel, the abnormality diagnosis apparatus comprising:
  an erroneous diagnosis preventing unit configured to prohibit or invalidate processes of the abnormality diagnosis until a specified time period has passed when a currently detected property of the fuel is different from a previously detected property of the fuel;
  wherein
  the fuel property detecting unit includes an alcohol concentration sensor detecting an alcohol concentration of the fuel.

2. An abnormality diagnosis apparatus according to claim 1, wherein
  the specified time period is established based on a time which is required for all of the fuel remaining in a fuel passage between the fuel property detecting unit and the fuel injector to be injected or on an integral fuel injection quantity.

3. An abnormality diagnosis apparatus according to claim 1, wherein the fuel property detecting unit is provided in the fuel tank.

4. An abnormality diagnosis apparatus for an internal combustion engine, including a fuel property estimating unit configured to estimate a fuel property based on an engine control condition which varies due to the fuel property, the abnormality diagnosis apparatus performing an abnormality diagnosis with respect to a specified object based on the fuel property, the abnormality diagnosis apparatus comprising:
  a nonvolatile memory unit configured to store the estimated fuel property; and
  an erroneous diagnosis preventing unit configured to invalidate processing data of the abnormality diagnosis which has been executed from a starting of the engine until it becomes apparent that a currently estimated fuel property is different from a previously estimated fuel property stored in the nonvolatile memory unit;
  wherein the fuel property estimating unit includes:
  an estimating unit configured to estimate a fuel property based a control condition of an air-fuel ratio feedback control which is executed based on an output of an exhaust gas sensor disposed in an exhaust passage of the engine; and
  a unit configured to use a previous fuel property stored in the memory unit as a current fuel property temporarily until the exhaust gas sensor is activated so that the air-fuel ratio feedback control can be executed.

5. An abnormality diagnosis apparatus according to claim 4, wherein
  the fuel property estimating unit includes a unit configured to prohibit an estimation of the fuel property until a specified time period has elapsed after engine is started.

6. An abnormality diagnosis apparatus according to claim 5, wherein
  the specified time period is established based on a time which is required for all of the fuel remaining in a fuel passage between a fuel tank and a fuel injector to be injected or on an integral fuel injection quantity.

7. An abnormality diagnosis apparatus for an internal combustion engine, including a fuel property estimating unit configured to estimate a fuel property based on an engine control condition which varies due to the fuel property, the abnormality diagnosis apparatus performing an abnormality diagnosis with respect to a specified object based on the fuel property, the abnormality diagnosis apparatus comprising:
  a nonvolatile memory unit configured to store the estimated fuel property; and
  an erroneous diagnosis preventing unit configured to invalidate processing data of the abnormality diagnosis which has been executed from a starting of the engine until it becomes apparent that a currently estimated fuel property is different from a previously estimated fuel property stored in the nonvolatile memory unit;
  wherein the fuel property estimating unit estimates an alcohol concentration of the fuel.

* * * * *